(12) United States Patent
Muschalek et al.

(10) Patent No.: US 10,561,765 B2
(45) Date of Patent: Feb. 18, 2020

(54) MEDICAL DEVICES COATED WITH SHAPE MEMORY POLYMER FOAMS

(71) Applicant: The Texas A&M University System, College Station, TX (US)

(72) Inventors: Rachael Muschalek, College Station, TX (US); Keith Hearon, Boston, MA (US); Landon D. Nash, Sunnyvale, CA (US); Duncan J. Maitland, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/746,574

(22) PCT Filed: Jul. 22, 2016

(86) PCT No.: PCT/US2016/043711
§ 371 (c)(1),
(2) Date: Jan. 22, 2018

(87) PCT Pub. No.: WO2017/019553
PCT Pub. Date: Feb. 2, 2017

(65) Prior Publication Data
US 2018/0214616 A1    Aug. 2, 2018

Related U.S. Application Data

(60) Provisional application No. 62/197,181, filed on Jul. 27, 2015.

(51) Int. Cl.
*A61L 31/10*    (2006.01)
*A61L 17/14*    (2006.01)
(Continued)

(52) U.S. Cl.
CPC ............. *A61L 31/10* (2013.01); *A61L 17/145* (2013.01); *A61L 27/34* (2013.01); *A61L 27/56* (2013.01);
(Continued)

(58) Field of Classification Search
None
See application file for complete search history.

(56) References Cited

U.S. PATENT DOCUMENTS 4,706,671 A    11/1987    Weinrib
4,994,069 A    2/1991    Ritchart et al.
(Continued)

FOREIGN PATENT DOCUMENTS

WO    2004016205 A2    2/2004
WO    2009013752 A2    1/2009

OTHER PUBLICATIONS

Brooks et al., "Effects of Isophorone Diisocyanate on the Hydrophobicity of Shape Memory Polymers," Aug. 9, 2013, College Station, Texas.
(Continued)

*Primary Examiner* — Chinessa T. Golden (57) ABSTRACT

An embodiment includes a system comprising: a substrate of a medical device; an un-foamed polyurethane coating directly contacting the substrate and fixedly attached to the substrate; a thermoset polyurethane shape memory polymer (SMP) foam, having first and second states, which directly contacts the polyurethane coating and fixedly attaches to the polyurethane coating; wherein the polyurethane coating fixedly attaches the SMP foam to the substrate. Other embodiments are described herein.

20 Claims, 8 Drawing Sheets

(51) Int. Cl.
   *A61L 27/34* (2006.01)
   *A61L 27/56* (2006.01)
   *A61L 31/14* (2006.01)
(52) U.S. Cl.
   CPC ......... *A61L 31/146* (2013.01); *A61L 2400/16* (2013.01)

(56) References Cited

U.S. PATENT DOCUMENTS

| | | |
|---|---|---|
| 5,045,601 A | 9/1991 | Capelli et al. |
| 5,049,591 A | 9/1991 | Hayashi et al. |
| 5,354,295 A | 10/1994 | Guglielmi et al. |
| 5,418,261 A | 5/1995 | Helsemans et al. |
| 5,522,836 A | 7/1996 | Palermo |
| 5,690,671 A | 11/1997 | McGurk et al. |
| 5,846,247 A | 12/1998 | Unsworth et al. |
| 6,086,599 A | 7/2000 | Lee et al. |
| 6,102,917 A | 8/2000 | Maitland et al. |
| 6,156,842 A | 12/2000 | Hoenig et al. |
| 6,238,403 B1 | 5/2001 | Greene, Jr. et al. |
| 6,458,127 B1 | 10/2002 | Truckai et al. |
| 6,551,340 B1 | 4/2003 | Konya et al. |
| 6,583,194 B2 | 6/2003 | Sendijarevic |
| 6,616,617 B1 | 9/2003 | Ferrera et al. |
| 7,308,738 B2 | 12/2007 | Barvosa-Carter et al. |
| 7,386,203 B2 | 6/2008 | Maitland et al. |
| 7,422,714 B1 | 9/2008 | Hood et al. |
| 7,611,524 B1 | 11/2009 | Maitland et al. |
| 7,744,604 B2 | 6/2010 | Maitland et al. |
| 7,828,790 B2 | 11/2010 | Griffin |
| 8,343,167 B2 | 1/2013 | Henson |
| 8,449,592 B2 | 5/2013 | Wilson et al. |
| 9,018,273 B2 | 4/2015 | Ito et al. |
| 9,051,411 B2 | 6/2015 | Wilson et al. |
| 10,010,327 B2 | 7/2018 | Wilson et al. |
| 2002/0010481 A1 | 6/2002 | Jayaraman |
| 2002/0142119 A1 | 10/2002 | Seward et al. |
| 2003/0028209 A1 | 2/2003 | Teoh et al. |
| 2003/0236533 A1 | 12/2003 | Wilson et al. |
| 2004/0030062 A1 | 2/2004 | Mather et al. |
| 2005/0021074 A1 | 1/2005 | Elliott |
| 2005/0038460 A1 | 2/2005 | Jayaraman |
| 2005/0043755 A1 | 2/2005 | Wilson et al. |
| 2005/0075405 A1 | 4/2005 | Wilson et al. |
| 2005/0085693 A1 | 4/2005 | Belson et al. |
| 2005/0165480 A1 | 7/2005 | Jordan et al. |
| 2005/0192621 A1 | 9/2005 | Wallace et al. |
| 2005/0228417 A1 | 10/2005 | Teitelbaum et al. |
| 2005/0267570 A1 | 12/2005 | Shadduck |
| 2005/0274454 A1 | 12/2005 | Extrand |
| 2005/0274455 A1 | 12/2005 | Extrand |
| 2006/0009785 A1 | 1/2006 | Maitland et al. |
| 2007/0016233 A1 | 1/2007 | Ferrera et al. |
| 2007/0104752 A1 | 5/2007 | Lee et al. |
| 2007/0135907 A1 | 6/2007 | Wilson et al. |
| 2008/0019657 A1 | 1/2008 | Maitland et al. |
| 2008/0051829 A1 | 2/2008 | Eidenschink et al. |
| 2008/0109057 A1 | 5/2008 | Calabria et al. |
| 2008/0114454 A1 | 5/2008 | Peterman et al. |
| 2008/0243167 A1* | 10/2008 | Paganon ................. A61F 5/003 606/192 |
| 2008/0269745 A1 | 10/2008 | Justin |
| 2009/0054918 A1 | 2/2009 | Henson |
| 2009/0093674 A1 | 4/2009 | Adams |
| 2009/0130391 A1 | 5/2009 | Taya |
| 2009/0248141 A1 | 10/2009 | Shandas et al. |
| 2009/0264835 A1 | 11/2009 | Schuermann |
| 2009/0280330 A1 | 11/2009 | Xie et al. |
| 2011/0015613 A1 | 1/2011 | Anzai |
| 2012/0158034 A1 | 6/2012 | Wilson et al. |
| 2013/0089576 A1 | 4/2013 | Maitland et al. |
| 2013/0317541 A1 | 11/2013 | Singhal et al. |
| 2014/0142207 A1* | 5/2014 | Singhal .............. A61B 17/0057 521/76 |
| 2014/0277057 A1 | 9/2014 | Ortega et al. |

OTHER PUBLICATIONS

The International Searching Authority, Written Opinion of the International Searching Authority and the International Search Report dated Oct. 13, 2016 in International Application No. PCT/US16/43711, eight pages.
Singhal, et al., "Ultra Low Density and Highly Crosslinked Biocompatible Shape Memory Polyurethane Foams," Journal of Polymer Science Part B: Polymer Physics, Mar. 4, 2012, pp. 724-737, vol. 50, Wiley Periodicals, Inc.
Small, et al., "Biomedical applications of thermally activated shape memory polymers," Journal of Material Chemistry, May 14, 2010, pp. 3356-3366, vol. 20, Issue 18.
Singhal, et al., "Low density biodegradable shape memory polyurethane foams for embolic biomedical applications," Acta Biomaterialia, Feb. 28, 2013, 35 pages.
European Patent Office, Extended European Search Report dated Jun. 29, 2015 for European Patent Application No. 11848981.4.
European Patent Office, Communication pursuant to Article 94(3) EPC dated Feb. 27, 2017 for European Patent Application No. 11848981.4.
Ayranci, et al., "Shape Memory Effect of a Thermoset Polymer and its Fiber Reinforced Composites," 18th International Conference on Composite Polymers, pp. 1-5.
Xie,"Recent advances in polymer shape memory," Polymer, Aug. 10, 2011, pp. 4985-5000, vol. 52, Elsevier Ltd.
Behl, et al, "Shape-memory polymers," Materials Today, Apr. 2007, vol. 10, No. 4, pp. 20-28, Elsevier Ltd.
Reddy, et al., "Bioinspired Surfaces with Switchable Adhesion," Advanced Materials, 2007, vol. 19, pp. 3833-3837, Wiley-VCH Verlag GmbH & Co., KGaA, Weinheim.
Hasan, et al., "Effects of Isophorone Diisocyanate on the Thermal and Mechanical Properties of Shape-Memory Polyurethane Foams," Macromolecular Chemistry and Physics, Macromolecular Journals, 2014, pp. 2420-2429, vol. 215, Wiley-VCH Verlag GmbH & Co., KGaA, Weinheim.
United States Patent and Trademark Office, Reply to Non-Final Office Action filed on Jan. 17, 2014 in U.S. Appl. No. 13/325,906.
United States Patent and Trademark Office, Reply to Final Office Action filed on Aug. 19, 2014 in U.S. Appl. No. 13/325,906.
United States Patent and Trademark Office, Reply to Non-Final Office Action filed on Jan. 7, 2016 in U.S. Appl. No. 13/325,906.
United States Patent and Trademark Office, Reply to Final Office Action filed on Sep. 8, 2016 in U.S. Appl. No. 13/325,906.
United States Patent and Trademark Office, Reply to Non-Final Office Action filed on Nov. 1, 2017 in U.S. Appl. No. 13/325,906.
United States Patent and Trademark Office, Reply to Non-Final Office Action filed on Jan. 17, 2017 in U.S. Appl. No. 13/325,906.
European Patent Office, Extended European Search Report dated Feb. 14, 2019 in European Patent Application No. 16831157.9.

* cited by examiner

MEDICAL DEVICES COATED WITH SHAPE MEMORY POLYMER FOAMS

PRIORITY CLAIM

This application claims priority to U.S. Provisional Patent Application No. 62/197,181 filed on Jul. 27, 2015 and entitled "Medical Devices Coated With Shape Memory Polymer Foams", the content of which is hereby incorporated by reference.

STATEMENTS AS TO RIGHTS TO INVENTIONS MADE UNDER FEDERALLY SPONSORED RESEARCH AND DEVELOPMENT

This invention was made with government support under R01EB000462 awarded by National Institutes of Health, National Institute of Biomedical Imaging and Bioengineering. The government has certain rights in the invention.

BACKGROUND

A cerebral aneurysm is a weakening of the neurovascular wall that allows localized dilation and ballooning of the artery. Aneurysms are susceptible to rupturing due to wall thinning, which causes an intracranial hemorrhage. It is estimated that 30,000 aneurysms rupture in the United States every year and approximately 3-5 million people in America have or will develop an aneurysm in their lifetime. Current aneurysm treatments include surgical clipping and the endovascular delivery of platinum coils to embolize the aneurysm. Surgical clipping includes a craniotomy and although proven effective, is extremely invasive. An endoscopic endonasal approach for aneurysm clipping has been successful, but it is also fairly invasive and requires pedicled nasoseptal flap reconstruction after the aneurysm clipping.

Endovascular embolization is now the preferred treatment for many patients. The current standard for embolization utilizes platinum coils to occlude the aneurysm and promote thrombogensis. Issues with platinum coils include material cost and a significant incidence of recanalization and retreatments due to coil packing over time. Hydrogel coated platinum wires were developed to reduce aneurysm recurrence rates and are the intermediary device between the platinum coil embolism treatments and shape memory polymer (SMP) coated treatments.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Applicant previously practiced a protocol for attaching SMP foams to a backbone wire. The protocol was to mechanically crimp and adhere the foam directly to the wire at both ends using epoxy, thus setting the secondary shape of the SMP around the wire. Using this process, Applicant determined a number of problems. Applicant determined the foams had a tendency to slip along the wire (if no epoxy or ineffective epoxy was used) and cause multiple problems during delivery of the device to the aneurysm site. Further, Applicant determined the use of epoxy could be detrimental to the device as a whole because of the possibility for a lack of biocompatibility. Additionally, Applicant determined the use of adhesive increases the minimum compressed diameter of the foam over the wire (which may complicate delivery of the foam into small areas, such as a patient's vasculature). In general, the process of adhering previously synthesized foam to a wire was problematic.

However, an embodiment includes a neurovascular embolism device that addresses these shortcomings. The embodiment uses ultra-low density polyurethane SMP foam adhered to a, for example, nitinol or polymer suture backbone to occlude the aneurysm. SMPs are a class of smart materials that are capable of deforming to a stable secondary shape (programmed state) and recovering to a primary form or state when exposed to a particular stimulus, such as heat. This shape memory property allows for the delivery of a compressed foam to the aneurysm site via micro-catheter and for consistent, high volume recoveries once positioned. The embodiment includes a process for attaching SMP foam to a backbone wire by synthesizing the foam directly over the nitinol wire or polymer suture backbone, while holding the current properties of the foam constant in the immediate vicinity of the wire. The specimen is then cut to the desired diameter using an Excimer Laser, resistive wire cutter, or biopsy punch. This eliminates the need to optimize the process of crimping the foam to the wire and alleviates multiple issues within the device design and fabrication, including foam slippage and detachment from the coil, and the use of an epoxy like adhesive.

In an embodiment a coating is added to a nitinol wire in order to facilitate the placement of the SMP foam to the wire. The embodiment aids in the production of a functional embolic device treatment using SMP foams synthesized directly onto a nitinol wire and shaped using an Excimer Laser. The axial length of the foam/wire device is approximately 12 cm in an embodiment but other embodiments include wires of 2, 5, 10, 15, 20, 25, 30 cm or more.

Embodiments are directed to a porous coating for a wire, wherein the porous coating comprises a porous, shape memory material. In certain embodiments, the porous coating is formed by coating the wire with a shape memory material and then curing the material to the wire. A further embodiment is directed to a medical device comprising a body and a porous coating secured to a surface of the body, wherein the porous coating comprises a porous, shape memory material. In certain embodiments, the porous coating is adapted to volumetrically expand so as to fill gaps between the coil and the wall of the blood vessel and to create volumetric occlusion between the medical device and the wall of the blood vessel. In such an embodiment, volumetric filling is achieved by the shape memory effect of the shape memory material, which causes blood flow stasis and embolization of vascular anatomy.

Another embodiment is directed to a method for providing therapy to a patient, the method comprising: providing a medical device comprising a body and a porous coating secured to a surface of the body, wherein the porous coating comprises a porous, shape memory material; inserting the medical device into the patient so that the porous coating volumetrically expands so as to fill gaps between the device body and the wall of the adjacent tissue to create volumetric filling between the medical device and the wall of the adjacent tissue. The interface of the porous coating and adjacent tissue is meant to promote cellular ingrowth to integrate and anchor the device to the tissue.

An embodiment is directed to the application of a SMP foam to a nitinol wire using a direct foaming process. In accordance with a process in an embodiment, the nitinol wire is coated with an optimized coating for proper foam adhesion, wetting, and stabilization of pores during the foaming process. The coatings used are selected from, but not limited to, the group consisting of a silicone coating, a hydrophilic coating (e.g., siloxane), a polytetrafluoroethylene (PTFE) coating, a thermoplastic polyurethane, and a thermoset neat polyurethane with a bulk chemical composition as the foam. The wires may be acid-etched or unetched prior to coating.

In an embodiment the coated wires are subjected to direct foaming by exposing the coated wires to a reaction mixture comprising at least one shape memory foam polymer and at least one foaming agent. In certain embodiments, the foaming agent is a blowing agent.

In an embodiment the reaction mixture is transferred to a container or vessel containing the coated wires. In certain embodiments, the coated wires are oriented axially to the direction of application of the foam. In other embodiments, the coated wires are oriented transversally to the direction of application of the foam.

Shape memory foam-coated wires of embodiments possess pore sizes and densities comparable to previously created foams. The ratio of bulk foam to FOW foam, excluding the mass of the substrate wire, is nearly one in many cases, indicating little to no change in the ultra low-density nature of the polymers. FOW pore sizes are comparable to their bulk foam counterparts, indicating little change in the nature of the foams.

WORKING EXAMPLES

Methods

Foam Synthesis

An established protocol for the synthesis of ultra low-density polyurethane SMP foams was used to create foam for device use. See Singhal et al (Controlling the Actuation Rate of Low-Density Shape-Memory Polymer Foams in Water; Macromol. Chem. Phys. 2013, 214, 1204-1214). An embodiment for foam synthesis involves combining the alcohols triethanolamine (TEA, Sigma Aldrich, St. Louis Mo.), and N,N,N',N'-Tetrakis (2-hydroxypropyl) ethylenediamine (HPED, Sigma Aldrich, St. Louis Mo.), in a ratio of 0.32-0.35 to isocyanates to form an NCO premix, or prepolymer. Isophorone diisocyanate (IPDI, TCI America, Tokyo, Japan) with a racemic mixture of 2,2,4-trimethyl-1, 6-hexamethylene diisocyanate and 2,4,4-trimethyl-1,6-hexamethylene diisocyanate (TMHDI TCI America, Tokyo, Japan) was used in varying compositions to create the polyurethane (PU) foams.

The range of chemical compositions for foam synthesis used in this experiment can be seen in Table 1.

TABLE 1

Isocyanate content of the five chemical compositions used in this experiment

| Chemical Composition | 1 | 2 | 3 | 4 | 5 |
| --- | --- | --- | --- | --- | --- |
| IPDI content | 0% | 5% | 10% | 15% | 20% |
| TMHDI Content | 100% | 95% | 90% | 85% | 80% |

An isocyanate premix of 32-35% alcohols was allowed to cure for two days in a programmed oven, in which the temperature was ramped to 50° C. and subsequently allowed to cool to room temperature. An alcohol premix, containing the balance of remaining OH monomers was created immediately before foaming to react with the excess isocyanates with a 0.96 OH/NCO ratio. The alcohol premix also contained catalysts BL-22 and T-131 as well as the surfactant, DC 5943, for pore stability. Water was added to the OH premix to serve as a chemical blowing agent for the foaming process. Table 2 shows the exact masses of agents added.

TABLE 2

Exact amounts of accessory chemicals for foaming process of all foam compositions created in this work

| | DC 5943 | BL-22 | T-131 | Enovate | Water |
| --- | --- | --- | --- | --- | --- |
| Target for one foam | 2.8 g | 0.253 g | 0.101 g | 7 mL | 0.917 g |

The OH premix and the NCO premix were combined and mixed for 10 seconds in a speed mixer (SpeedMixer DAC 150 FVZ-K, Flacktek, Landrum, SC), after which the physical blowing agent, Enovate, was added and the polymer was mixed again for 10 additional seconds. The reaction mixture was carefully transferred into a large bucket containing the coated wires, which were previously positioned in the bucket, and placed in an oven. As the foam reacted, it experienced about 30× volume expansion and took the primary shape of the container it was reacting in. The foam was allowed to react for 20 minutes at 90° C., after which time the foam was removed from the oven and allowed to cool to room temperature under a fume hood.

Once cooled, the buckets were slightly deformed to release the foams from the container. The wires attached through small holes in the bottom were released, the tape discarded. At this point the foams were simply lifted out of the bucket. The foams were cut in half using the Proxxon Thermocut Hotwire Cutter.

Coating Optimization and Adhesion

Some embodiments include an optimized coating for proper foam adhesion. Test coatings were ordered from Coatings2Go.com and tested on multiple samples. Without any etching process, a silicone coating, a hydrophilic coating (e.g., siloxane), and a hydrophobic polytetrafluoroethylene (PTFE) coating were applied onto the 0.0035" diameter nitinol wire using a KimWipe. This process was repeated for acid etched wires, which were etched using a mixture of 1:3 ratio of 6M nitric acid and 6M hydrochloric acid. Lastly, a thermoset neat polymer with the same bulk chemical composition as the foam was used as a wire coating. Bare, untreated, and acid etched wires were used as controls for foam adhesion.

Neat coatings were created inside a humidity-controlled chamber in order to reduce isocyanate-reactions with ambient moisture. The four monomers were mixed in stoichiometric amounts with varying IPDI content congruent to the foam to be created. The monomer target values for all compositions can be seen in Table 3 below.

TABLE 3

Stoichiometric amounts of monomers for varying IPDI Content in Neat Polymers

| Components | Target for 1 foam (g) | Scale | Total target value (g) |
|---|---|---|---|
| 0% IPDI | | | |
| HPED | 9.191 | 0.25 | 2.298 |
| TEA | 3.080 | 0.25 | 0.770 |
| TMHDI | 19.729 | 0.25 | 4.932 |
| IPDI | 0.000 | 0.25 | 0.000 |
| 5% IPDI | | | |
| HPED | 9.175 | 0.25 | 2.294 |
| TEA | 3.074 | 0.25 | 0.769 |
| TMHDI | 18.710 | 0.25 | 4.677 |
| IPDI | 1.041 | 0.25 | 0.260 |
| 10% IPDI | | | |
| HPED | 9.159 | 0.25 | 2.290 |
| TEA | 3.069 | 0.25 | 0.767 |
| TMHDI | 17.694 | 0.25 | 4.424 |
| IPDI | 2.078 | 0.25 | 0.520 |
| 15% IPDI: | | | |
| HPED | 9.143 | 0.25 | 2.286 |
| TEA | 3.063 | 0.25 | 0.766 |
| TMHDI | 16.682 | 0.25 | 4.170 |
| IPDI | 3.112 | 0.25 | 0.778 |
| 20% IPDI: | | | |
| HPED | 9.127 | 0.25 | 2.282 |
| TEA | 3.058 | 0.25 | 0.765 |
| TMHDI | 15.673 | 0.25 | 3.918 |
| IPDI | 4.142 | 0.25 | 1.036 |

Once the chemicals were massed and measured, the polymer solution was then mixed for one minute, checked for homogeneity, and mixed again for one minute. The wires to be coated were strung into a rectangular frame structure, and the polymer coatings were wiped on by hand using a Kim-Wipe.

Wire Orientation

To attain ideal foaming, Applicant determined the wire orientation also required optimization in some embodiments. Wires were strung in one bucket transversely to the foaming direction, while the second bucket had wires axial to the foam. This tested the interactions of the foam and wires to determine the least disruptive orientation to foaming. Once determined, an attachment to the foaming vessel was created in order to optimize foam/wire adherence that maintained the stability of the wire.

Microscope Imaging

Microscope imaging was used to determine the homogeneity of the foam surrounding the wire and quantitative data such as density and pore size. Dry volume expansion was then used to further quantify the homogeneity of the foams. After foam synthesis, the wires were cut out of the foam using a Proxxon Thermocut Hotwire Cutter to remove extraneous foam. The sample was then imaged using a Leica long-range microscope with Jenoptic camera system and the foam morphology surrounding the wire was used to determine the useful length, with a goal of 12 cm. 12 cm was a parameter derived from the length of the final geometry of the device, a coil of nitinol wire in the aneurysm.

Density Calculations

Figure 2:
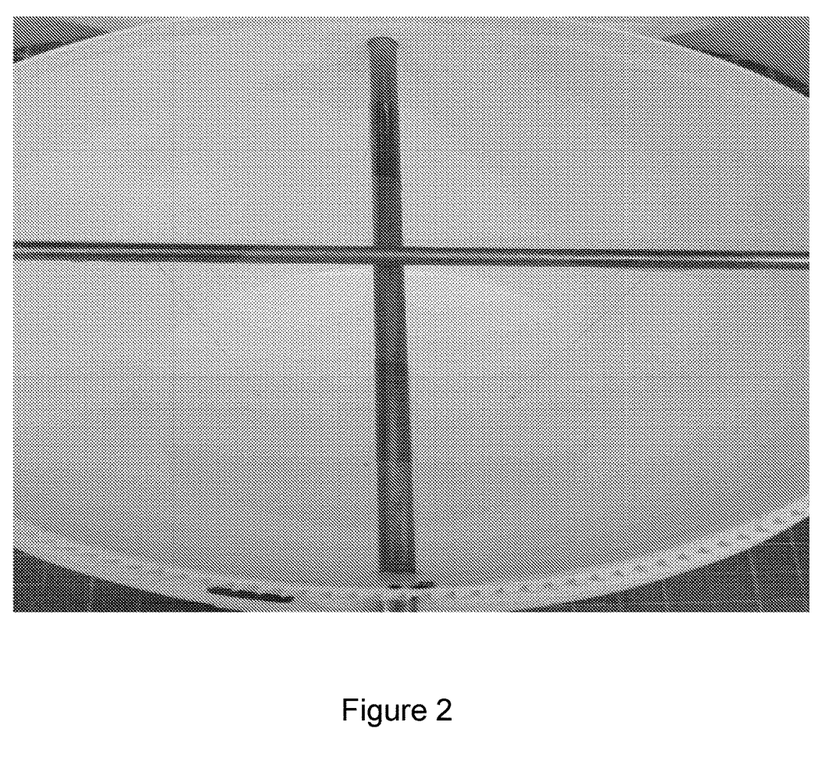
FIG. 2 includes vertically oriented substrates in an embodiment (i.e., substrate long axis located generally parallel to path of expanding foam).

The ratio of the foam density surrounding the wire to the density of the bulk foam was measured to determine foam homogeneity in the vicinity of the wire. Bulk foam density was calculated by cutting three small squares from the center of the foam, far away from the wires to ensure minimal interference with the general structure and pores of the samples. The length, width, and height of each of the three squares were measured three times and the averages of each dimension were taken. These averages were used to calculate the volume of the foam sample. The sample was then massed and the density was found using Equation 1.

$$\rho = m/V \qquad \text{Equation (1)}$$

Where ρ is the density, m is the mass, and V is the volume. This process was then repeated for samples taken within 2 mm of the wire for three wires in the foam. The process used to measure the cube volume described above was repeated and each cube was massed. The calculated density was then averaged and then the bulk foam density was divided by the average wire-foam density, resulting in the ratio of the two foam types, as described by Equation 2.

$$\text{Density Ratio} = \rho\text{Bulk}/\rho\text{Wire} \quad \text{Equation (2)}$$

Where Density Ratio is the reported value, ρBulk is the bulk foam density (where bulk foam refers to the foam after initial foaming and separate and apart from obstacles such as wires or other substrates, such as FIG. 2), and ρWire is the wire foam density.

Pore Size Calculations

Cell images were taken using a Leica long-range microscope with Jenoptic camera system from a sample of foam approximately one cell thick cut transversely to the axis of foaming. The diameter of a specific cell was measured from the collected images, and the diameter of 15 cells was used for the analysis. For non-circular cells, diameters were taken at the longest point between two walls. Calculations assume perfectly circular cell sizes. Pore sizes were calculated using Equation 3:

$$\text{Pore Size} = \frac{\pi}{4}d^2 \quad \text{Equation (3)}$$

Where d is the measured diameter of the cell.

Volume Recovery in Air

Cylindrical samples with a diameter of 6 mm and a height of 4 cm were cut from the bulk foam, making sure that the wire was embedded along the axis of the sample. The foams were radially crimped using an ST150-42 Machine Solutions stent crimper to the smallest possible diameter. The secondary morphology was set by maintaining the samples at 100° C. while in the primary shape for 20 minutes, then crimping to the smallest possible diameter and subsequently cooling the samples back to room temperature. An image was taken using the Leica long-range microscope with Jenoptic camera system and analyzed for the diameter using Image J software. The samples were actuated at 100° C. for 20 minutes in an oven, and allowed to cool to room temperature. Once cooled, the samples were again imaged and analyzed for the final diameter. The volume recovery was calculated using Equation 4.

$$V_E = (D_r/D_c)^2 \quad \text{Equation (4)}$$

Where $V_E$ is the volume expansion, $D_r$ is the recovered diameter, and $D_c$ is the crimped diameter.

This was repeated for 5 samples.

Scanning Electron Microscope Images

Scanning Electron Microscope (SEM) images were taken of two samples of wire. The first sample was the uncoated, 0.0035" nitinol backbone wire. The second sample was the same nitinol wire with the addition of a neat polymer coating. The resulting images were analyzed with ImageJ Software to determine the overall change in diameter caused by the addition of the neat polymer coating.

Results

Foam Synthesis

Foam Synthesis was completed on a range of chemical compositions (See Table 1). It was noted that as IPDI content increased (15% IPDI and 20% IPDI), the successful length of foam along the wire was lower when holding all other variables constant. The viscosity of the prepolymer increased with increasing IPDI content and resulted in a more viscous reaction mixture than lower IPDI concentrations as the foam progressed up the wire. To account for the increase in viscosity, the ratio of OH/NCO prepolymer was decreased from 0.35 to 0.32. This change produced for a longer successful foam length along the wire as determined by qualitative imaging.

Figure 1:
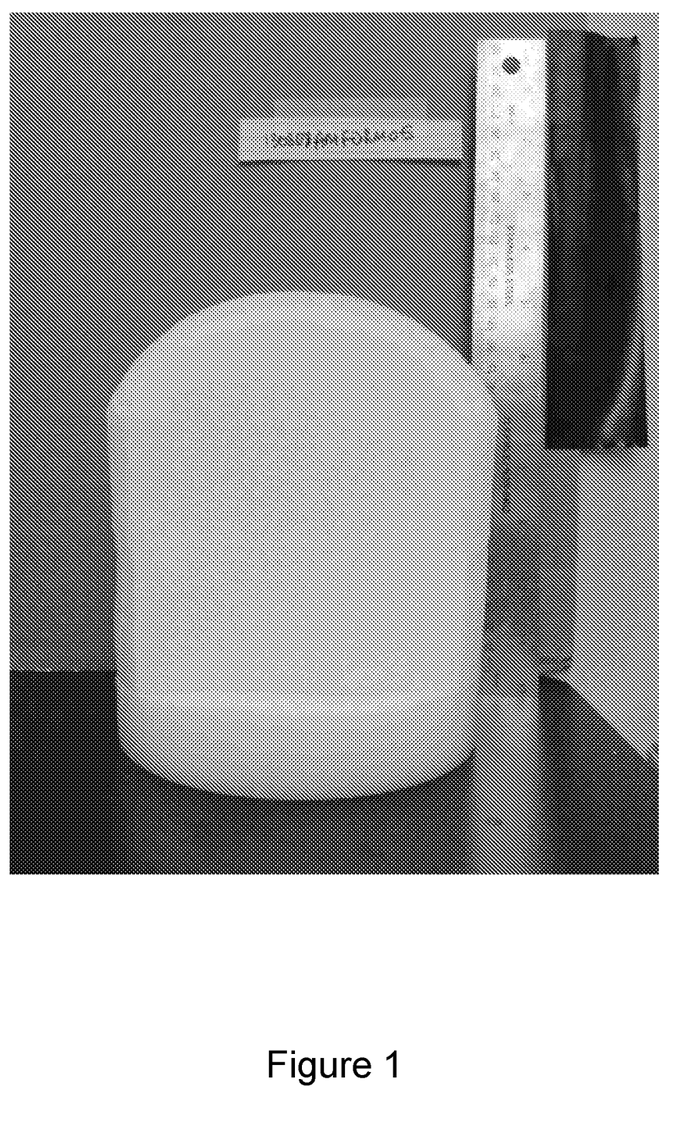
FIG. 1 includes a bulk foam in an embodiment.

It was also discovered that the lower IPDI content foams (0% and 5% IPDI) should have a shorter mixing time than higher IPDI content foams after the addition of the Enovate. The lower IPDI content lends to a lower viscosity prepolymer compared to higher IPDI concentrations. The less viscose foam mixture required less mixing to achieve homogeneity, and rapidly expanded in size. The original 10 second mixing time was reduced to 5 seconds, and this change resulted in greater bulk homogeneity in foam composition, as shown in FIG. 1.

Two different methods of securing wires were tested, shown in FIG. 2, in order to determine the best method to attach wires to a foaming vessel. Applicant determined that the top of the foaming vessel needed to secure the coated wires, eliminating as much lateral motion as possible and to allow gaseous escape during the foaming reaction. Attaching wires to the bucket handle allowed for forward/backward movement from the handle, and was not adequate for our purposes. The concept was tedious and wasteful because it required taping spatulas to the top of the foaming bucket. From the given constraints, and the desire to be able to foam over many wires at once, the final structure, as seen in FIG. 2, was created with the goal of securing the coated wires to the foaming vessel.

1 mm diameter holes were cut in the bottom of the 2 L bucket, 1.5" from the center (halfway between center and outer diameter) at 90° angles from one another. This allowed four wires to be fed through the bottom of the bucket and taped down using Kapton heat-resistant tape. The wires were then pulled taught through the bucket and attached to the steel bars, seen in FIG. 2, using the Kapton tape.

Coating Optimization and Adhesion

Multiple coatings were tested in order to optimize foam-wire adhesion, including uncoated (as a control), PTFE, Hydrophillic, silicone, and neat SMP. When uncoated wires were placed in the foaming vessel and foam was synthesized directly onto them, large caverns in the foams surrounding the wires were created. This was due to contrasting chemical compositions of the nitinol wire and PU foams. The silicone, PTFE, and hydrophilic coatings were used to coat the 0.0035" wire following the directions provided by the company. The homogeneity of the foam is severely compromised in the immediate vicinity of the wire for silicone, PTFE, and hydrophilic coatings. For example, density near the wire is far greater than bulk foam density. From this, Applicant determined in some embodiments the coating of the wire should have an almost identical chemical composition as the foam. Therefore thermoset neat polymer was used as a coating.

Figure 3:
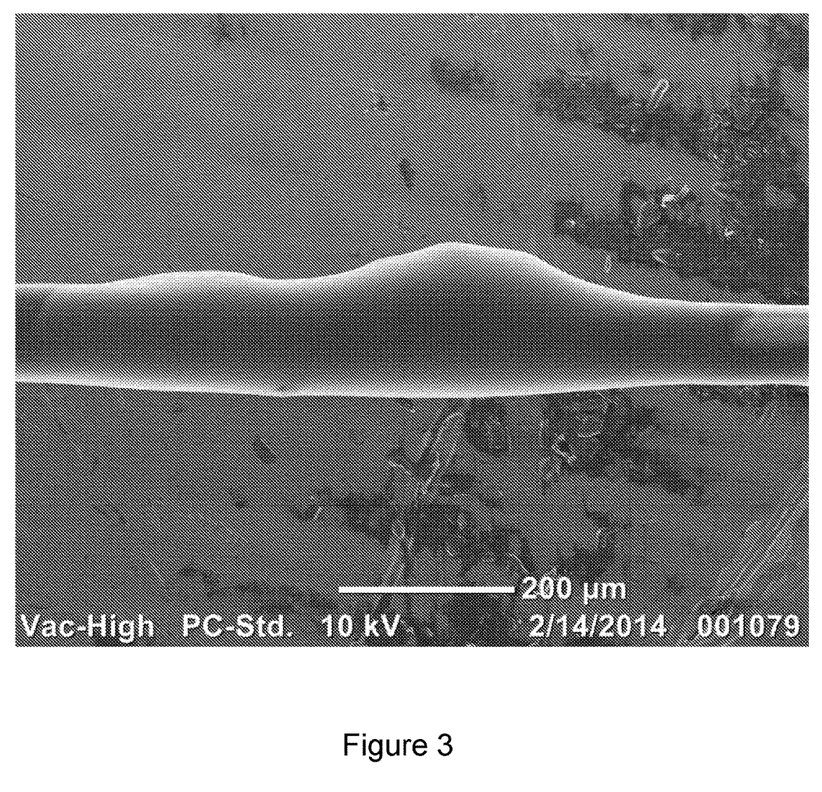
FIG. 3 includes a polymer coated substrate in an embodiment.

An SEM image of the neat polymer coated wire can be seen in FIG. 3. The polymer formed an uneven distribution of the polymer along the wire. Applicant determined that uneven coatings actually increased homogenous foam adhesion due to the expansion of the foam as it progressed up the wire.

Additionally, the uneven adhesion caused a varying change in diameter of the wire from the neat polymer. The original diameter of the wire was 0.0035" whereas the highest recorded diameter after two neat polymer coatings was 0.0069". This was almost double the diameter of the wire and could cause significant issues when crimping the foam around the wire because the crimped device diameter should ideally be under 0.016' to accommodate the dimensions of human microcatheters.

Wire Orientation

Figure 4:
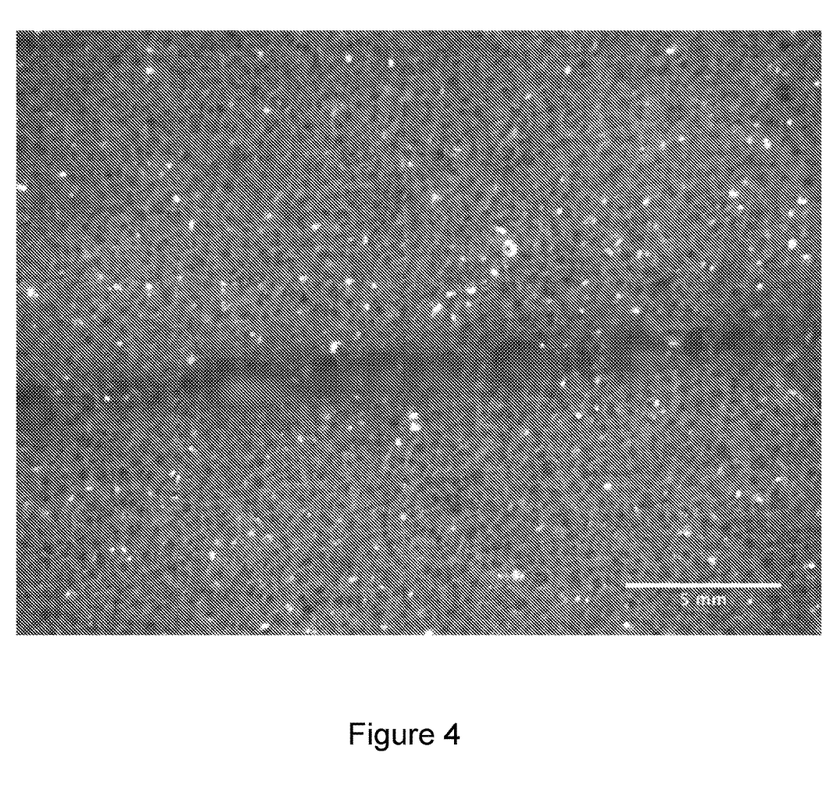
FIG. 4 shows a top view (with foam rising towards viewer of figure) of void caused by a horizontally oriented substrate (i.e., substrate long axis located generally orthogonal to path of expanding foam).
Figure 5:
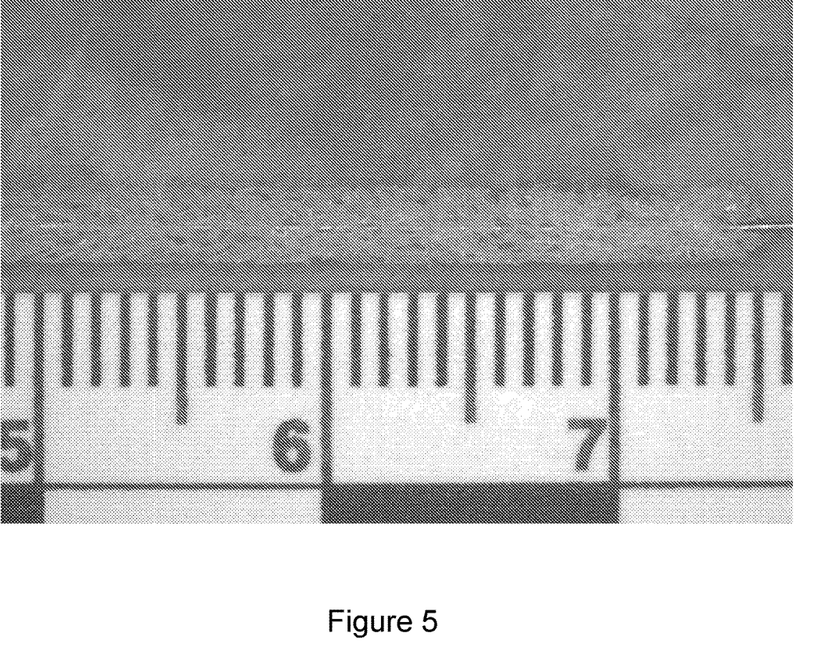
FIG. 5 includes a foam over wire (FOW) in an embodiment.

At least 4 attempts at wire orientation inside the buckets were foamed and it was determined by inspection that the transverse wires disrupted the foaming process significantly more than the vertical wires. There was a higher probability that the foam would split immediately above transverse placed wires, resulting in poor foam coverage above the wire, as shown in FIG. 4. FIG. 4 is a perspective taken just above the foam showing a cavity in the "wake" or side of substrate opposite the side that was initially contacted by foam. However, there was no such void when the substrate was oriented vertically with the substrate directly contacting the foam on all sides of the substrate (e.g., FIG. 2 set up). In other words, the vertically oriented wire had adequate adhesion and little foam disruption compared to the previous coating used. FIG. 5 shows the overall FOW structure. The specimen seen in FIG. 5 was cut to a diameter of 2.5 mm from the bulk foam using an Excimer Laser.

Density Calculations

The results of the density calculations are summarized in Table 4 below.

TABLE 4

Results of foam density calculations

| Composition | Bulk Density (g/cm³) | FOW Density (g/cm³) | Ratio |
|---|---|---|---|
| 0% IPDI | 0.0107 | 0.0113 | 1.0622 |
| 5% IPDI | 0.0108 | 0.0109 | 1.0141 |
| 10% IPDI | 0.0127 | 0.0111 | 1.0207 |
| 15% IPDI | 0.0120 | 0.0111 | 0.9662 |
| 20% IPDI | 0.0092 | 0.0093 | 1.0075 |

The bulk density was the foam density calculated near the center of the foam, where no wires are present. The FOW density was calculated using foam taken within 2 mm of the wire. The ratio calculated is the FOW density to the bulk density. The majority (4 out of 5) of the density ratios were greater than one, implying that the foam surrounding the wires was slightly denser than the density of standard foams of the same composition. This was to be expected since the wire causes an imperfection in the foaming area, causing the foam to congregate more around the wire. Maintaining low density in the vicinity of the wire was of paramount importance because it relates to smaller device diameters when crimping. Since the ratio of densities was only slightly larger than one, this parameter was met.

Pore Size Calculations

Figure 6:
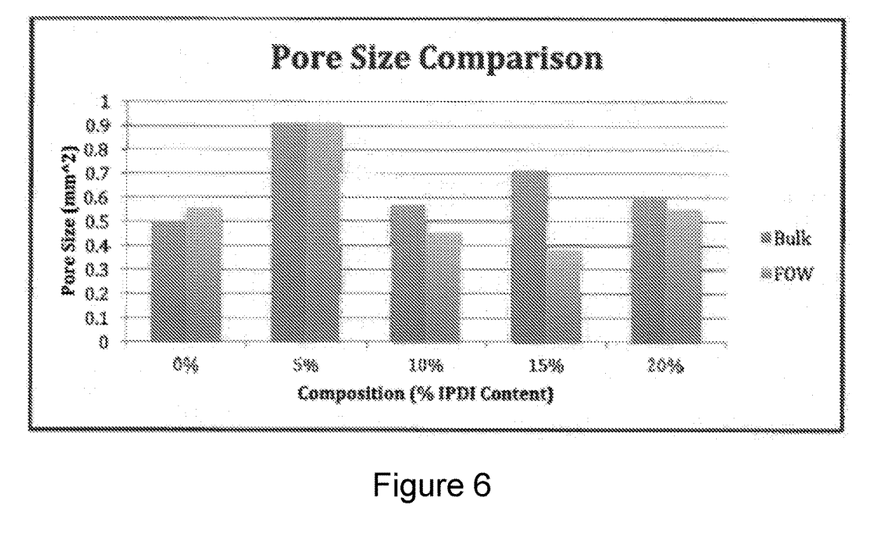
FIG. 6 addresses pore size for FOW and bulk foam in an embodiment.

The data acquired from the pore size experiments are summarized in FIG. 6. The pore size data indicates that there were slightly smaller pores in the FOW samples for the majority of compositions, with the largest difference being the 15% IPDI composition. However, Applicant noted that this composition had irregular data among all the experiments performed. Overall, as expected, pore size decreased slightly in the vicinity of the wire. However since this decrease was minimal, it shouldn't have a significant impact on the device as a whole.

Volume Recovery in Air

Figure 7:
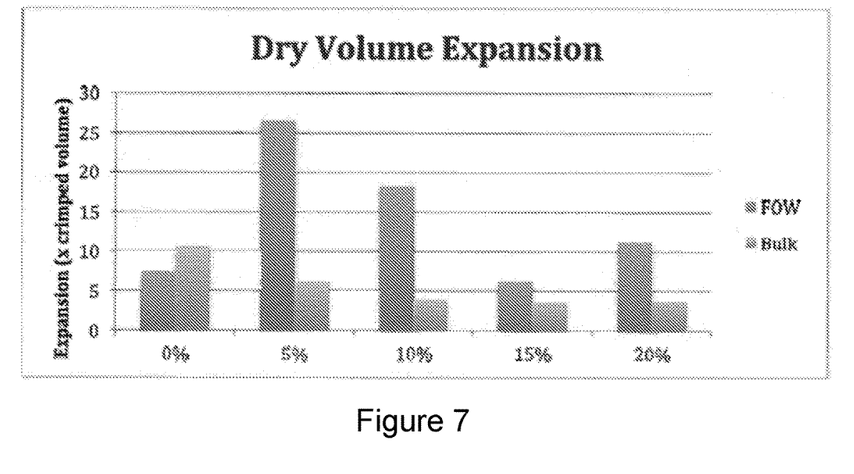
FIG. 7 addresses dry volume expansion for FOW and bulk foam in an embodiment.

The results of the volume recovery experiments in air are summarized in FIG. 7. The data suggested large variability with possibly of decreasing volume recovery with increasing IPDI content. The data was skewed possibly due to the variability of foam quality around wire, and the position of the wire relative to the center of the foam. When cutting the foam with the biopsy punch, it was difficult to place the wire directly in the middle of the cylinder. The data would have been more accurate if all the samples were cut using an Excimer laser, ensuring the nitinol backbone wire was centered within the foam cylinder. The dry volume expansion data also suggested that adhered foam-wire samples may have better volume expansion than their bulk foam counter-part samples, which is excellent for use of this technology in the overall device. It is also important to note that dry volume expansion behavior was not entirely representative of the clinical uses of this material. Future expansion tests will be conducted in a heated water bath to better represent the aqueous vascular environment.

The following examples pertain to further embodiments.

Example 1 includes a system comprising: a substrate of a medical device; an un-foamed polyurethane coating directly contacting the substrate and fixedly attached to the substrate; a thermoset polyurethane shape memory polymer (SMP) foam, having first and second states, which directly contacts the polyurethane coating and fixedly attaches to the polyurethane coating; wherein the polyurethane coating fixedly attaches the SMP foam to the substrate.

While polyurethane examples (for the coating and the foam) are mentioned herein, other types of foams and/or coatings may be used including, for example and without limitation, polycarbonate, polyamide, polyurea, polyester, polycaprolactone, polyolefin, or combinations thereof.

The substrate may include a polymer suture, a metal backbone coil or wire (platinum, nitinol, nichrome), the exterior ring of a prosthetic heart valve, the exterior surface of a stent graft, a face of a water or air filter, a surface of a safety helmet, and the like. In other words, examples are not limited to medical devices, much less embolic foams for aneurysms.

By fixedly attaching the foam to the substrate, the coating alleviates many problems Applicant identified (e.g., a foam that slides along a backbone can be difficult to place in an aneurysm or atrial appendage or anatomical void and the like). For example, a polymer coating having the same or similar chemistry as the foam helps prevent the rising foam from contacting a foreign object (e.g., an uncoated nitinol wire) and bunching or coalescing around the object (e.g., where cells in foam collapse at the wire interface forming a dense region of foam (as compared to the bulk foam) that may lose flexibility and become unsuitable for certain applications like manipulation through tortuous vasculature of a patient).

Example 2 includes the system of claim 1, wherein the polyurethane coating is a thermoplastic.

Example 3 includes the system of claim 1, wherein the polyurethane coating is a cured thermoset.

Thus, embodiments allow, for example, thermoplastic or thermoset coatings.

Example 4 includes the system of claim 1, wherein the polyurethane coating has a chemical composition equal to a chemical composition of the SMP foam.

Example 5 includes the system of claim 1, wherein the polyurethane coating and the SMP foam both include N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED.

For example, the coating may include a neat polymer that is un-foamed yet still have the same chemical structure or constituents as the foamed polymer.

Example 6 includes the system of claim 1, wherein the polyurethane coating and the SMP foam both include N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

Example 7 includes the system of claim 1, wherein the polyurethane coating and the SMP foam both include N,N,N',N'-tetrakis (2-hydroxypropyl) ethylenediamine (HPED), Glycerol, pentanediol, and hexamethylene diisocyanate (HDI).

Example 8 includes the system of claim 1, wherein the polyurethane coating is more hydrophobic than siloxane and less hydrophic than polytetrafluoroethylene (PTFE).

Applicant has determined such a level of hydrophobicity helps the rising foam adequately couple to the coating without forming a dense foam area at the substrate/foam interface.

Example 9 includes the system of claim 1, the SMP foam includes cells and a majority of the cells include unequal major and minor axes and the major axes generally align with each other.

For example, in an embodiment the cells are elliptical with a major axis generally parallel (+/−15 degrees) to the long axis of the substrate, such as the long axis of the vertical substrate of the wires of FIG. 2. This would not be true for the instance where the wire is orthogonal to the foam path, such as FIG. 4. In an embodiment, the elliptical cells are within 2 mm of the substrate.

Example 10 includes the system of claim 9, wherein substrate includes a major axis unequal to a minor axis and the major axis of the substrate generally aligns with the major axes of the majority of the cells.

Example 11 includes the system of claim 1, the SMP foam includes cells and a majority of the cells are isotropic in shape.

In other embodiments, the cells are not as described in Example 9. In some embodiments the cells are elliptical within 2 mm of the substrate but isotropic more than 2 mm from the substrate. 2 mm is a demarcation used for explanation and can be 1, 3, 4, 5, 6 mm or more in other embodiments.

Example 12 includes the system of claim 1, wherein the substrate is included in a member selected from the group comprising: embolic coil, stent, stent graft, polymer suture, wire, heart valve, and tissue scaffold.

Example 13 includes the system of claim 1, wherein: the polyurethane coating directly contacts the SMP foam along a first maximum length; and the polyurethane coating directly contacts the substrate along a second maximum length that is at least as long as the first maximum length.

For example, in FIG. 2 the foam would envelope and adhere along the entire length of the wire substrate. Due to masking, the polymer coating may cover the majority of the wire but other portions of the coating may be masked such that they do not adhere to foam. Such masking may allow for placing foam at intervals on the substrate and the like. Regardless, in such a case the foam need not contact every portion of the coating but the coating may still ensure the foam is secured along the entire length of the foam. For example, for an embolic foam a backbone may have enough polymer coating such that the entire length of the embolic foam fixedly adheres to the backbone, thereby facilitating foam placement. Embodiments may include situations where the foam is longer than the polymer coating or vice versa. Portions of the substrate may be masked and connect to neither polymer coating nor foam.

Example 14 includes the system of claim 13, wherein the first maximum length is at least 2 cm and the substrate includes a wire that is less than 0.0020" in diameter.

In other embodiments the length is 4, 6, 8, 10, 12, 14, 16, 18, 20 cm or more and/or 0.001", 0.003", 0.004" 0.005", 0.006" diameter or more.

Example 15 includes the system of claim 1, wherein: the SMP foam has inner and outer portions; the inner portion is no more than 2 mm thick, measured orthogonal to the substrate, and directly between the outer portion and the polyurethane coating; the inner portion has a first foam density and the outer half portion has a second foam density; a ratio of the first foam density to the second foam density is less than 1.1.

Other embodiments include a ratio of 0.8, 0.9, 1.2, 1.4, 1.6 and the like. For example, the center of a column or portion of foam may have a density immediately adjacent the substrate that is similar to the density further removed from the substrate.

Example 16 includes the system of claim 1, wherein: the SMP foam has inner and outer portions; the inner portion is no more than 2 mm thick, measured orthogonal to the substrate, and directly between the outer portion and the polyurethane coating; the inner portion has a first foam density and the outer portion has a second foam density and both of the first and second foam densities are less than 0.06 g/cm3.

Other embodiments include a density less than 0.04, 0.08, 0.1, and 0.5 g/cm$^3$.

Example 17 includes the system of claim 1, wherein: the SMP foam has inner and outer portions; the inner portion is no more than 2 mm thick, measured orthogonal to the substrate, and directly between the outer portion and the polyurethane coating; the inner portion has a first average cell diameter and the outer half portion has a second average cell diameter that is greater than the first average cell diameter.

Example 18 includes a method comprising: coating a substrate of a medical device with an un-foamed polyurethane coating that directly contacts the substrate and fixedly attaches to the substrate; forming a mixture by combining N,N,N',N'-tetrakis (2-hydroxypropyl) ethylenediamine (HPED), and at least two members selected from the group consisting of: triethanolamine (TEA), and hexamethylene diisocyanate (HDI), trimethylhexamethylenediamine (TMHDI), Glycerol, and pentanediol; locating the polyurethane coated substrate adjacent the mixture; foaming the mixture into a monolithic foam that expands towards the polyurethane coated substrate, directly contacts the polyurethane coated substrate, substantially surrounds the polyurethane coated substrate, and fixedly attaches to the polyurethane coated substrate; separating the monolithic foam into a first portion of the foam contacting the polyurethane coated substrate and a remaining bulk portion of the foam; and forming the first portion of the foam into a primary state and a programmed state to form a shape memory polymer (SMP) foam.

Figure 8:
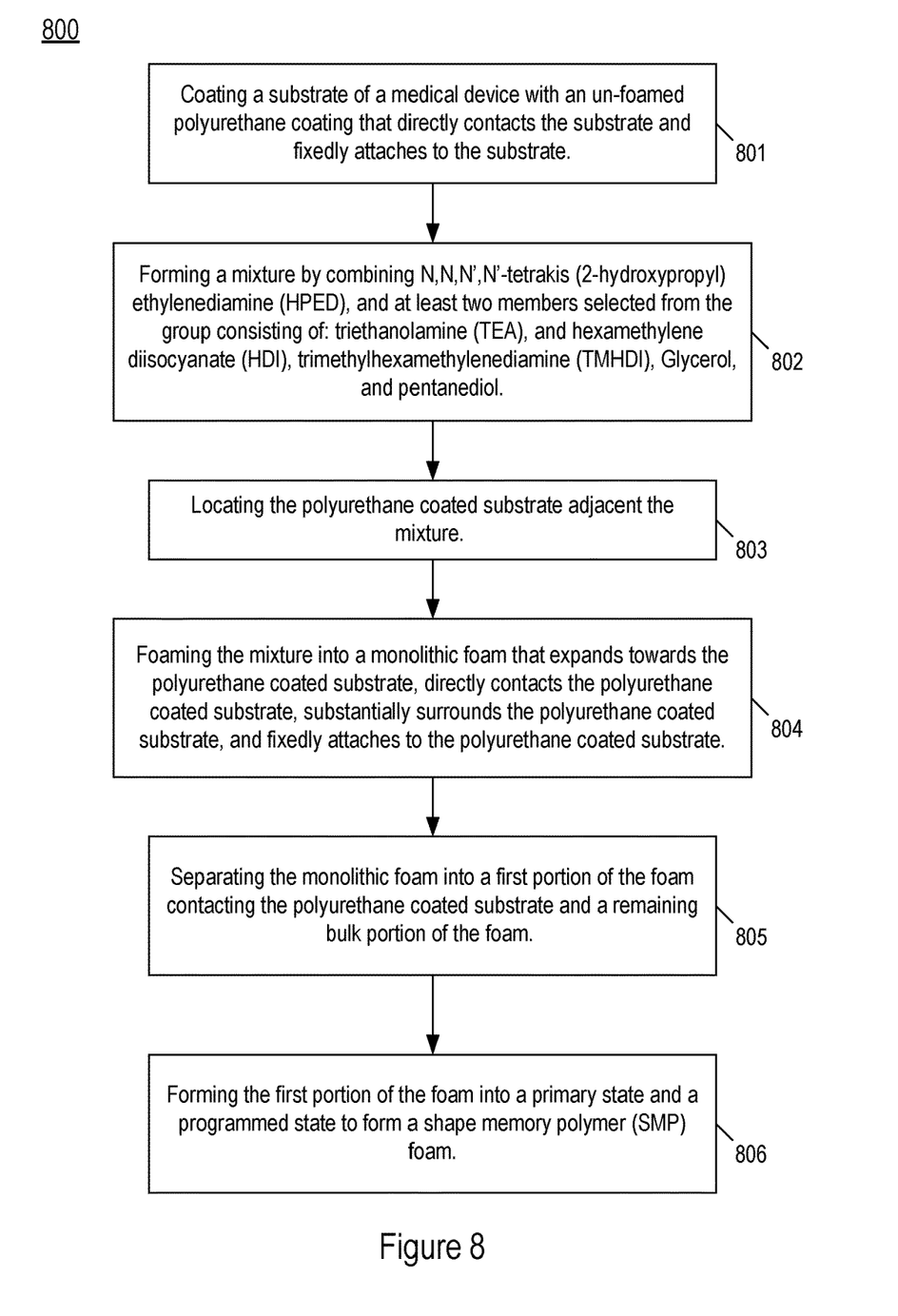
FIG. 8 includes a process in an embodiment.

FIG. 8 includes method 800. Block 801 includes coating a substrate of a medical device with an un-foamed polyurethane coating that directly contacts the substrate and fixedly attaches to the substrate. Block 802 includes forming a mixture by combining N,N,N',N'-tetrakis (2-hydroxypropyl) ethylenediamine (HPED), and at least two members selected from the group consisting of: triethanolamine (TEA), and hexamethylene diisocyanate (HDI), trimethylhexamethylenediamine (TMHDI), Glycerol, and pentanediol. Block 803 includes locating the polyurethane coated substrate adjacent the mixture. For example, see FIG. 2 where the mixture would be in the bottom of the bucket and would move upwards along the substrate. Block 804 includes foaming the mixture into a monolithic foam that expands towards the polyurethane coated substrate, directly contacts the polyurethane coated substrate, substantially surrounds the polyurethane coated substrate, and fixedly attaches to the polyurethane coated substrate. Block 805 includes separating the monolithic foam into a first portion of the foam contacting the polyurethane coated substrate and a remaining bulk portion of the foam. Block 806 includes forming the first portion of the foam into a primary state and a programmed state to form a shape memory polymer (SMP) foam.

Example 19 includes the method of claim 18, wherein foaming the mixture into a monolithic foam comprises expanding the monolithic foam to first contact a proximal portion of the polyurethane coated substrate, then a middle portion of the polyurethane coated substrate, and then a distal portion of the polyurethane coated substrate.

Example 20 includes the method of claim 19, wherein foaming the mixture into a monolithic foam comprises simultaneously surrounding the monolithic foam in a plane orthogonal to a long axis of the polyurethane coated substrate.

Example 21 includes the method of claim 20, wherein the un-foamed polyurethane coating comprises HPED, and at least two members selected from the group consisting of: TEA, HDI, TMHDI, Glycerol, and pentanediol.

Example 1a includes a porous coating for a wire or coil, wherein the porous coating comprises a porous, shape memory material, wherein the porous coating is adapted to volumetrically expand as to fill gaps between the device body and the wall of the adjacent tissue and to create volumetric filling between the medical device and the adjacent tissue.

Example 2a includes a porous coating according to example 1 wherein the porous coating is formed by coating the wire with a shape memory material and then heating on to the wire.

Example 3a includes a medical device comprising a body and a porous coating secured to a surface of the body, wherein the porous coating comprises a porous, shape memory material.

Example 4a includes the medical device according to example 1 wherein the volumetric expansion is caused by the shape memory effect of the shape memory material.

Example 5a includes the medical device according to example 1 wherein the volumetric filling by the porous coating causes an interface with the adjacent tissue and promotes cellular ingrowth.

Example 6a includes a method for providing therapy to a patient, the method comprising: providing a medical device comprising a body and a porous coating secured to a surface of the body, wherein the porous coating comprises a porous, shape memory material; inserting the medical device into the patient so that the porous coating expands against the adjacent tissue so as to fill gaps between the device body and the wall of the adjacent tissue and to promote tissue integration between the medical device and the wall of the blood vessel.

Example 7a includes the method according to example 6 wherein the volumetric expansion is created by the shape memory effect of the shape memory material.

Example 8a includes the method according to example 6 wherein the volumetric expansion of the porous coating causes embolization of an aneurysm.

Example 9a includes a method of applying a shape memory polymer to a nitinol wire using a direct foaming process.

Example 10a includes the method of example 9, wherein the nitinol wire is coated with a coating application to the application of the shape memory polymer foam.

Example 11a includes the method of example 10, wherein the coating is selected from, but not limited to, the group consisting of a silicone coating, a hydrophilic coating, a polytetrafluoroethylene (PTFE) coating, a polyurethane, and a thermoset neat polymer with the same bulk chemical composition as the foam.

Example 12a includes the method of example 11, wherein the wire is acid-etched prior to coating.

Example 13a includes the method of example 11, wherein the wire is unetched prior to coating.

Example 14a includes the method of example 11 wherein, the wire is subjected to direct foaming by exposing the wire to a reaction mixture comprising at least one shape memory foam polymer and at least one foaming agent.

The foregoing description of the embodiments has been presented for the purposes of illustration and description. It is not intended to be exhaustive or to limit the embodiments to the precise forms disclosed. This description and the claims following include terms, such as left, right, top, bottom, over, under, upper, lower, first, second, etc. that are used for descriptive purposes only and are not to be construed as limiting. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the embodiments be limited not by this detailed description, but rather by the claims appended hereto.

What is claimed is:

1. A system comprising:
   a substrate of a medical device;
   an un-foamed polyurethane coating directly contacting the substrate and fixedly attached to the substrate;
   a thermoset polyurethane shape memory polymer (SMP) foam, having first and second states, which directly contacts the polyurethane coating and fixedly attaches to the polyurethane coating;
   wherein the polyurethane coating fixedly attaches the SMP foam to the substrate;
   wherein the SMP foam includes cells and a majority of the cells include unequal major and minor axes and the major axes generally align with each other;
   wherein the polyurethane coating is more hydrophobic than siloxane and less hydrophobic than polytetrafluoroethylene (PTFE).

2. The system of claim 1, wherein the polyurethane coating is a thermoplastic.

3. The system of claim 1, wherein the polyurethane coating is a cured thermoset.

4. The system of claim 1, wherein the polyurethane coating has a chemical composition equal to a chemical composition of the SMP foam.

5. The system of claim 1, wherein the polyurethane coating and the SMP foam both include N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED.

6. The system of claim 1, wherein the polyurethane coating and the SMP foam both include N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

7. The system of claim 1, wherein the polyurethane coating and the SMP foam both include N,N,N',N'-tetrakis (2-hydroxypropyl) ethylenediamine (HPED), Glycerol, pentanediol, and hexamethylene diisocyanate (HDI).

8. The system of claim 1, wherein the substrate includes a major axis unequal to a minor axis and the major axis of the substrate generally aligns with the major axes of the majority of the cells.

9. The system of claim 1, wherein the substrate is included in at least one of an embolic coil, a stent, a stent graft, a polymer suture, a wire, a heart valve, a tissue scaffold, or combinations thereof.

10. The system of claim 1, wherein:
the polyurethane coating directly contacts the SMP foam along a first maximum length; and
the polyurethane coating directly contacts the substrate along a second maximum length that is at least as long as the first maximum length.

11. The system of claim 10, wherein the first maximum length is at least 2 cm and the substrate includes a wire that is less than 0.0020" in diameter.

12. The system of claim 1, wherein:
the SMP foam has inner and outer portions;
the inner portion is no more than 2 mm thick, measured orthogonal to the substrate, and directly between the outer portion and the polyurethane coating;
the inner portion has a first foam density and the outer half portion has a second foam density;
a ratio of the first foam density to the second foam density is less than 1.1.

13. The system of claim 1, wherein:
the SMP foam has inner and outer portions;
the inner portion is no more than 2 mm thick, measured orthogonal to the substrate, and directly between the outer portion and the polyurethane coating;
the inner portion has a first foam density and the outer portion has a second foam density and both of the first and second foam densities are less than 0.06 g/cm$^3$.

14. The system of claim 1, wherein:
the SMP foam has inner and outer portions;
the inner portion is no more than 2 mm thick, measured orthogonal to the substrate, and directly between the outer portion and the polyurethane coating;
the inner portion has a first average cell diameter and the outer half portion has a second average cell diameter that is greater than the first average cell diameter.

15. A system comprising:
a substrate of a medical device;
an un-foamed polyurethane coating directly contacting the substrate and fixedly attached to the substrate;
a thermoset polyurethane shape memory polymer (SMP) foam, having first and second states, which directly contacts the polyurethane coating and fixedly attaches to the polyurethane coating;
wherein:
the polyurethane coating fixedly attaches the SMP foam to the substrate;
the polyurethane coating has a chemical composition equal to a chemical composition of the SMP foam;
the SMP foam has inner and outer portions;
the inner portion is no more than 2 mm thick, measured orthogonal to a major axis of the substrate, and directly between the outer portion and the polyurethane coating;
the SMP foam includes cells and in a cross-section taken orthogonal to the major axis of the substrate, the inner portion has a first average cell diameter and the outer portion has a second average cell diameter that is greater than the first average cell diameter; wherein the polyurethane coating is more hydrophobic than siloxane and less hydrophobic than polytetrafluoroethylene (PTFE).

16. The system of claim 15, wherein:
the polyurethane coating and the SMP foam both include at least one of N,N,N',N'-tetrakis (2-hydroxypropyl) ethylenediamine (HPED), triethanolamine (TEA), or combinations thereof;
the polyurethane coating and the SMP foam both include hexamethylene diisocyanate (HDI).

17. The system of claim 16, wherein:
in the cross-section a majority of the cells included in the outer portion include unequal major and minor axes and the major axes are generally parallel with each other;
the major axis of the substrate is unequal to a minor axis of the substrate and the major axis of the substrate is generally parallel with the major axes of the majority of the cells included in the outer portion.

18. A method comprising:
coating a substrate of a medical device with an un-foamed polyurethane coating that directly contacts the substrate and fixedly attaches to the substrate;
forming a mixture by combining N,N,N',N'-tetrakis (2-hydroxypropyl) ethylenediamine (HPED), and at least two of: triethanolamine (TEA), hexamethylene diisocyanate (HDI), trimethylhexamethylenediamine (TMHDI), Glycerol, pentanediol, or combinations thereof;
locating the polyurethane coated substrate adjacent the mixture;
foaming the mixture into a monolithic foam that expands towards the polyurethane coated substrate, directly contacts the polyurethane coated substrate, substantially surrounds the polyurethane coated substrate, and fixedly attaches to the polyurethane coated substrate;
separating the monolithic foam into a first portion of the foam contacting the polyurethane coated substrate and a remaining bulk portion of the foam; and
forming the first portion of the foam into a primary state and a programmed state to form a shape memory polymer (SMP) foam;
wherein the SMP foam includes cells and a majority of the cells include unequal major and minor axes and the major axes generally align with each other; wherein the polyurethane coating is more hydrophobic than siloxane and less hydrophobic than polytetrafluoroethylene (PTFE).

19. The method of claim 18, wherein foaming the mixture into a monolithic foam comprises expanding the monolithic foam to first contact a proximal portion of the polyurethane coated substrate, then a middle portion of the polyurethane coated substrate, and then a distal portion of the polyurethane coated substrate.

20. The method of claim 19, wherein:

foaming the mixture into a monolithic foam comprises simultaneously surrounding the monolithic foam in a plane orthogonal to a major axis of the polyurethane coated substrate;

the un-foamed polyurethane coating comprises HPED, and at least two of: TEA, HDI, TMHDI, Glycerol, pentanediol, or combinations thereof.

* * * * *

UNITED STATES PATENT AND TRADEMARK OFFICE
CERTIFICATE OF CORRECTION

PATENT NO. : 10,561,765 B2  
APPLICATION NO. : 15/746574  
DATED : February 18, 2020  
INVENTOR(S) : Rachael Muschalek et al.

Page 1 of 1

It is certified that error appears in the above-identified patent and that said Letters Patent is hereby corrected as shown below:

In the Claims

Column 15:  
Line 34, Claim 12 "outer half portion" should be --outer portion--;  
Line 52, Claim 14 "outer half portion" should be --outer portion--.

Signed and Sealed this  
Second Day of June, 2020

Andrei Iancu  
*Director of the United States Patent and Trademark Office*